(12) United States Patent
Jeejeebhoy

(10) Patent No.: US 6,455,243 B1
(45) Date of Patent: Sep. 24, 2002

(54) NUTRITIONAL ASSESSMENT BY MEASURING MITOCHONDRIAL COMPLEX ACTIVITY

(76) Inventor: Kursheed Jeejeebhoy, 69 Boulton Drive, Toronto, Ontario (CA), M4V 2V5

( * ) Notice: Subject to any disclaimer, the term of this patent is extended or adjusted under 35 U.S.C. 154(b) by 0 days.

(21) Appl. No.: 09/719,451

(22) PCT Filed: Jun. 14, 1999

(86) PCT No.: PCT/CA99/00551

§ 371 (c)(1),
(2), (4) Date: Feb. 16, 2001

(87) PCT Pub. No.: WO99/66064

PCT Pub. Date: Dec. 23, 1999

(30) Foreign Application Priority Data

Jun. 12, 1998 (CA) .............................. 2240588

(51) Int. Cl.⁷ .............................. C12Q 1/00; C12Q 1/26
(52) U.S. Cl. .............................. 435/4; 435/25
(58) Field of Search .............................. 435/4, 7.21, 25

(56) References Cited

U.S. PATENT DOCUMENTS 6,013,858 A * 1/2000 Wallace et al.
6,080,788 A * 6/2000 Sole et al.

OTHER PUBLICATIONS

O Blin et al. Mitochondrial respiratoary failure in skeletal muscle form patients with parkinson's disease and multiple system atrophy Journal of the Neurological Sciences 125 1994 95–101.*

C Antozzi MD et al. Late–onset riboflavin–responsive myopathy with combined multiple acyl coenzyme a dehdrogenase and respiratory chain deficiency Neurology 1994;44:2153–2158.*

N. Barr'oso et al. Respiratory Chain Enzyme Activities in Lymphocytes from Untreated Patients with Parkinson Disease Clin Chem. 39/4, 667–669 1993.*

Biological Abstracts, Philidelphia PA USA; abstract No. PREV199900294999, abstract XP002120033, Apr. 1999.

Biological Abstracts, Philidelphia PA USA; abstract No. PREV199900318397, abstract XP002120034, Apr. 1999.

Copy of the International Search Report dated May 11, 1999.

* cited by examiner

Primary Examiner—Robert A. Schwartzman
Assistant Examiner—Bronwen M. Loeb
(74) Attorney, Agent, or Firm—Sim & McBurney

(57) ABSTRACT

According to a first aspect of the invention, a method of detecting malnutrition in a mammal is provided. The method includes the steps of: (a) measuring the activity in the mammal of one of more complexes selected from the group consisting of Complex I, Complex II, and Complex III; and (b) determining if the level of activity is below the level of activity of the complexes in a normal control sample. According to a second aspect of the invention, the use of Complex I is disclose for nutritional assessment of a mammal. According to a third aspect of the invention, the use of Complex II is disclosed for nutritional assessment of a mammal. According to a fourth aspect of the invention, the use of Complex III is disclosed for nutritional assessment of a mammal. According to a fifth aspect of the invention, a kit for nutritional assessment of a mammal is provided, comprising one or more reagents for measuring the activity in the mammal of one or more complexes selected from the group consisting of Complex I, Complex II, and Complex III.

11 Claims, 15 Drawing Sheets

NUTRITIONAL ASSESSMENT BY MEASURING MITOCHONDRIAL COMPLEX ACTIVITY

BACKGROUND OF THE INVENTION

1. Field of the Invention

This invention relates to nutritional assessment, and in particular to a method of nutritional assessment by measuring Complex I, II, and III activity, as well as use of these compounds for nutritional assessment.

2. Description of the Prior Art

It is known in the prior art that lack of or excess intake of nutrients results in a change in the amount of body fat, lean tissue[1] and plasma proteins Accordingly, prior art methods of nutritional assessment have been based on changes in both body composition and plasma proteins. However, these prior art methods are not able to differentiate whether the loss of body fat and leant tissue results from lack of intake of nutrients, or from some other cause not related to nutrition, such as disease.

Accordingly, there is a need for a nutritional assessment which is capable not only of determining malnutrition, but also whether the cause of the malnutrition is a lack of intake of nutrients.

SUMMARY OF THE INVENTION

It is an object of the invention to provide a method of nutritional assessment which is capable of determining malnutrition, and whether malnutrition is caused by lack of nutrient intake.

According to a first aspect of the invention, a method of detecting malnutrition in a mammal is provided. The method comprises the steps of:

(a) measuring the activity in the mammal of one or more complexes selected from the group consisting of Complex I, Complex II, and Complex III; and (b) determining if the level of activity is below the level of activity of the complexes in a normal control sample.

According to a second aspect of the invention, the use of Complex I is disclosed for nutritional assessment of a mammal.

According to a third aspect of the invention, the use of Complex II is disclosed for nutritional assessment of a mammal.

According to a fourth aspect of the invention, the use of Complex III is disclosed for nutritional assessment of a mammal.

According to a fifth aspect of the invention, a kit for nutritional assessment of a mammal is provided, comprising one or more reagents for measuring the activity in the mammal of one or more complexes selected from the group consisting of Complex I, Complex II, and Complex III.

Further features of the invention will be described or will become apparent in the course of the following detailed description.

BRIEF DESCRIPTION OF THE DRAWINGS

In order that the invention may be more clearly understood. the preferred embodiment thereof will now be described in detail by way of example, with reference to the accompanying drawings, in which.

DESCRIPTION OF THE PREFERRED EMBODIMENT

Figure 1:
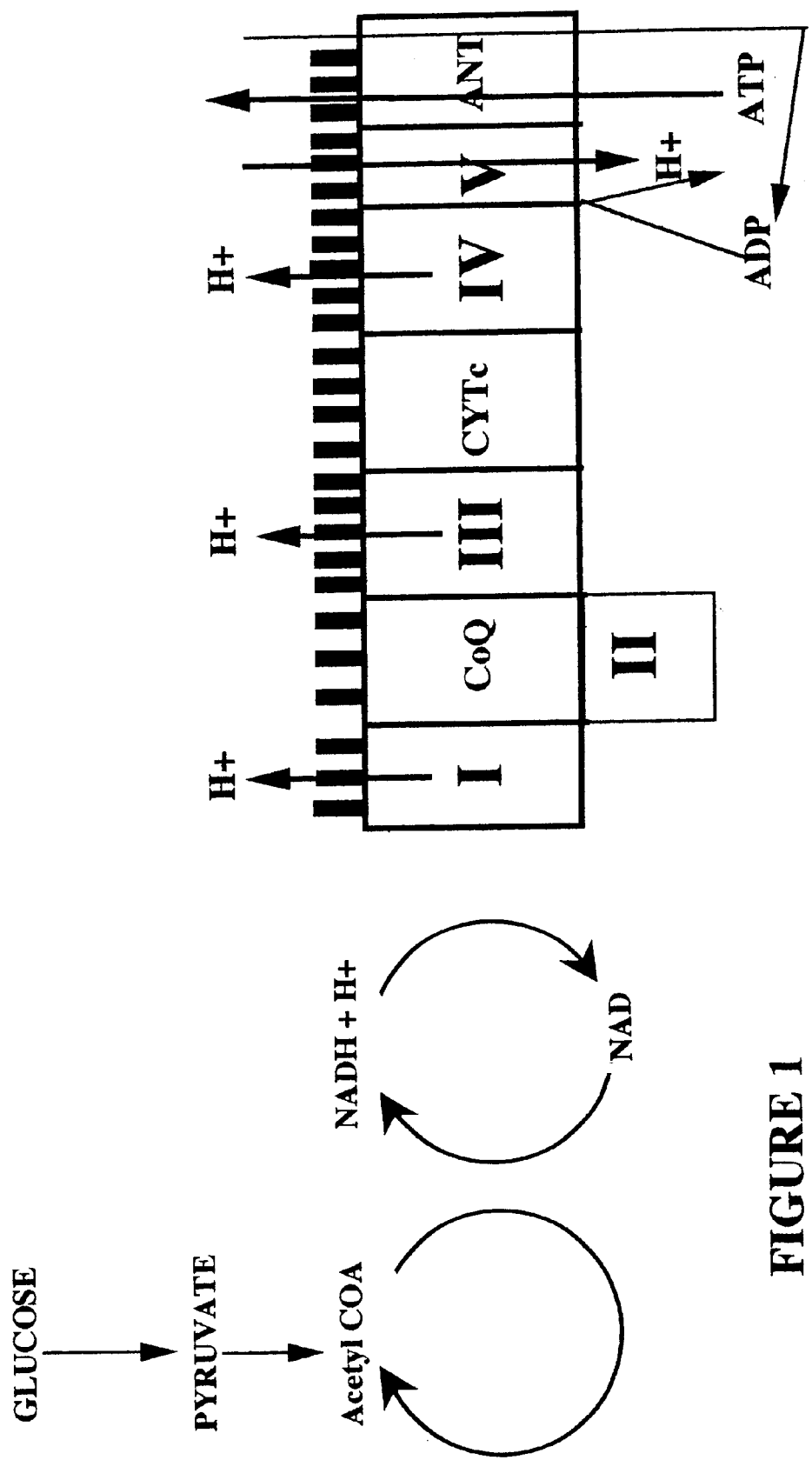
FIG. 1 is a diagram of electron transport chain.

Feeding wasted individuals results in a gain of the multiple elements in lean tissue[2] as well as of body fat. One of the elements responding to nutrient intake is body potassium, which has been used as an index of body cell mass[3], the metabolically active component of me lean tissue. Studies[4,5,6,7,8] have shown that in contrast to body nitrogen, body potassium responds rapidly to feeding by both oral and intravenous routes. Cell ion uptake, an energy dependent process, occurs earlier than protein synthesis during nutritional support. furthermore, studies have shown, that hypocaloric feeding results in reduced muscle membrane potential and concentration of intracellular $K^{+9,10}$. The changes are specifically related to nutrient deprivation, because they were not reversed by potassium supplementation. Since five molecules of ATP are required for the incorporation of one molecule of amino acid into protein, and 77% of the free energy change of ATP hydrolysis is used to maintain the Na-K gradient across the cell membrane[11,12] nutritional support initially alters cell energetics. Studies[13,14] have shown that hypocaloric feeding significantly reduced the ratio of phosphocreatine(PCR) to ATP, increased free ADP (FADP) levels and reduced the effective free energy change of ATP hydrolysis (dGATp). In subsequent studies, it was shown that the influence of hypocaloric feeding on muscle energetics was entirely due to protein-clorie deficiency and not to electrolyte or micronutrient deficiency. In slowly contracting muscle, studies have showed that the rephosphorylation of ADP was slower in muscle from rats fed a hypocaloric diet. Finally, by the use of saturation-transfer and inversion-transfer. studies have shown that hypocaloric feeding altered the relationship of FADP and ATP turnover. In hypocaloric rats oxidative phosphorylation was less responsive to a rise in FADP levels. Accordingly, mitochondrial response to FADP is altered by hypocaloric feeding. The findings of Ardawi et al[15] showing reduced oxygen consumption by the mitochondria of hypocalorically fed rats supported the NMR data above.

O'Brien et al[16], using heart muscle showed for the first time that calcium release, reuptake and ATP cycling, all energy dependent functions, were markedly disturbed by hypocaloric feeding.

Changes in Muscle Cell Energetics as Determined by $^{31}$P-NMR Spectroscopy($^{31}$P-NMRS)

Studies[13] of muscle using $^{31}$P-NMRS in the resting state, have shown that phosphocreatine (PCr) falls, while the free energy change for ATP hydrolysis (Delta $G_{ATP}$) and free ADP (FADP)levels rise in hypocalorically fed rats. The change in the Delta $G_{ATP}$, while small, was of a magnitude which has been shown in the heart to be associated with marked changes in systolic pressure. Furthermore it was shown that exposing skinned muscle fibers[17] to a lower Delta $G_{ATP}$, comparable to that seen in fatigued muscle (in this paper Debta $G_{ATP}$ is referred to as affinity,[18]) resulted in a reduction of maximum force compared to fibers exposed to a higher Delta $G_{ATP}$. The effect of non-fatiguing simulation on oxidative phosphorylation in hypocaloric muscle was examined, as well as changes in muscle energetics during and between tetanic contractions at a very slow rate of 1 tetanus per minute, to allow full oxidative recovery of energy substrates. It was shown that hypocaloric feeding reduces both the rate of rephosphorylation and the fall in Delta $G_{ATP}$ (Delta $G_{ATP}$ is a negative value) during post-stimulation rest. Using saturation transfer, it has been shown that hypocaloric feeding results in an altered response of the mitochondria to FADP stimulation. Relevant to the above results is the control of mitochondrial respiration, for which the following factors have been recognized. First, when NADH generation is no longer rate limiting[19], a rise in free ADP (FADP) stimulates respiration by its translocation[20] into the mitochondria While $Ca^{2+}$ regulates oxidative phosphorylation by activating dehydrogenases, FADP control of mitochondria is altered by hypocaloric feeding. Furthermore, this effect is due to protein calorie deficiency per se.

The focus of the present invention is on the effect of hypocalonc feeding and refeeding ad libitum and with specific nutrients on the ADP control of oxidative phosphorylation.

Summary of Mitochondrial Electron Transfer, Oxidative Phosphorylation and its Application to Nutritional Assessment Mitochondrial Complexes and Electron flow.

All energy producing reactions, including glycolysis and the Tricarboxylic acid (TCA)cycle, generate reducing equivalents in the form of NADIH and reduced flavins. These reducing agents are ultimately oxidized by oxygen through a chain of oxidoreduction reactions occurring in complexes residing in the inner mitochondrial membrane, as shown in FIG. 1. With each of these reactions, electrons or hydrogen atoms (which are equivalent to a proton +electron) are transferred from a reducing agent (which becomes oxidized) to an oxidizing agent (which becomes reduced). This series of transfers constitutes the electron chain. At each reaction there is an associated efflux of protons, creating a high energy state which drives ATF synthesis. The electron transfer is organized into four complexes: the ATP synthase complex and an adenine nucleotide transporter[21]. Two substrates Coenzyme Q10 (CoQ10) and cytochrome c carry electrons between complexes. The oxidation reduction reactions which occur are known and are summarized in FIG. 2. NADH and succinate are oxidized by Complex I and II respectively and the electron acceptor is CoQ10 which becomes reduced. The reduced CoQ10 is oxidized by Complex III and the electron acceptor is cytochrome c which is reduced. These are equilibrium reactions but finally reduced cytochrome c is oxidized by Complex IV using oxygen and forming water. These processes create a proton gradient across the inner mitochondrial membrane which is used to drive ATP synthesis by Complex V (F0F1 ATPase).

Measurement of Complex Activity

Figure 2:
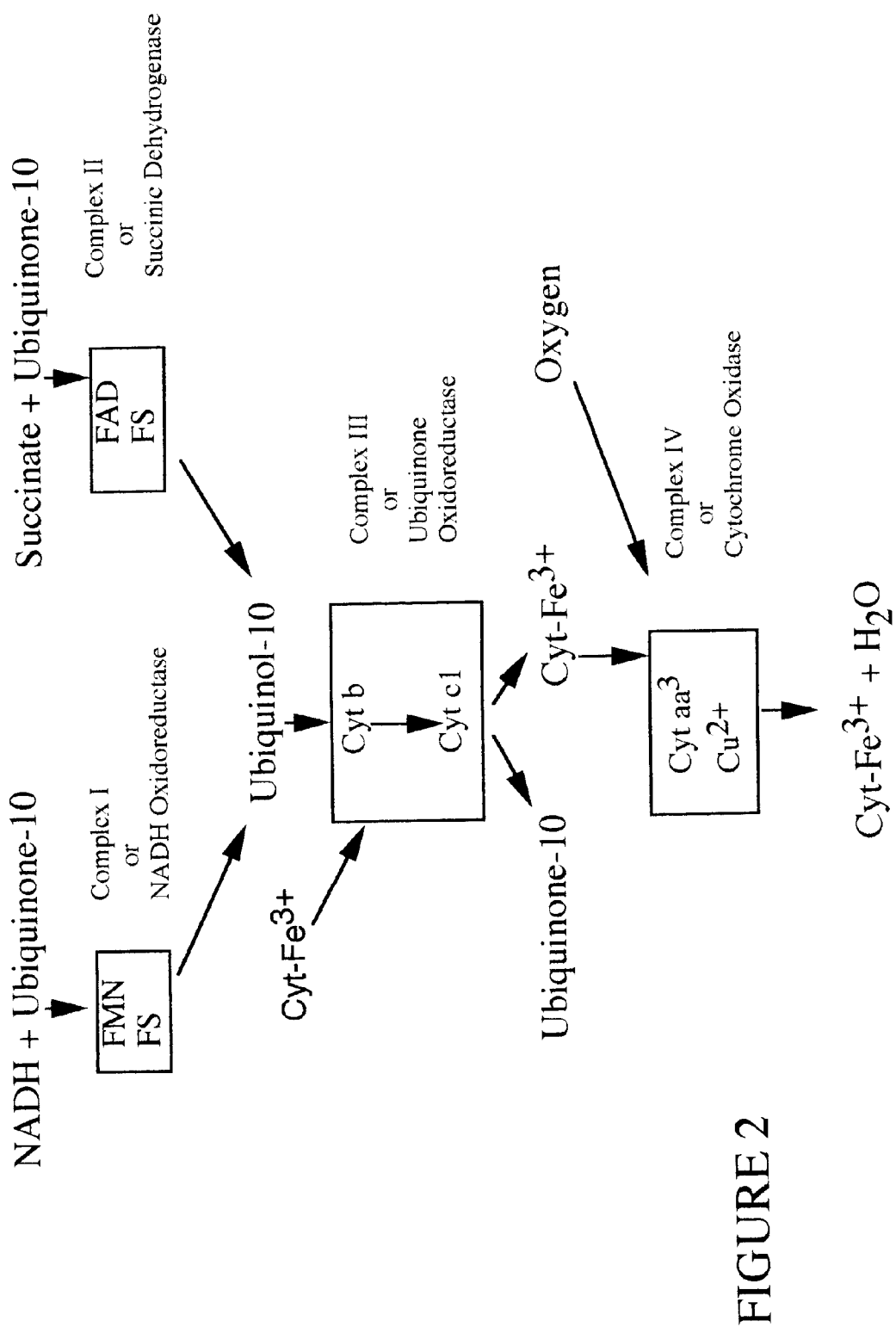
FIG. 2 shows the details of the chemical reaction during electron transport, FMN=Flavin mononucleotide, FS=iron-sulfur center, cyt=cytochrome.

In order to measure complex activity, it is necessary to isolate the reaction of each complex. This is done by: (i) using optimal methods for releasing the complex from the inner mitochondrial membrane; (ii) using specific electron donors and acceptors for the complex concerned, as shown in FIG. 2: and (iii) showing that the reaction is inhibited by specific inhibitors of the compiex. These inhibitors are rotenone for Complex I, antimycin for Complex III, and cyanide for Complex IV. These factors have been studied by Birch-Machin et al and others[22,23].

Molecular Biology of Mitochondria.

The Mitochondria contain a closed circular, double-stranded DNA of about 16.5 kb. Both strands are transcribed and encode for 13 polypeptide in addition to 12s and 14s ribosomal RNAs and 8 transfer RNAs[24]. The mitochondrial DNA encodes for 7 out of 25 subunits of Complex I, nil for Complex II, 1 out of 8 for Complex III, and 3 out of 10 for Complex 4. In addition, all tRNAs involved in mitochondrial protein synthesis are encoded in the mitochondria. The mitochondrial proteins synthesized in the cytoplasm are imported into the mitochondria and assembled into mature enzyme systems[25].

Figure 3:
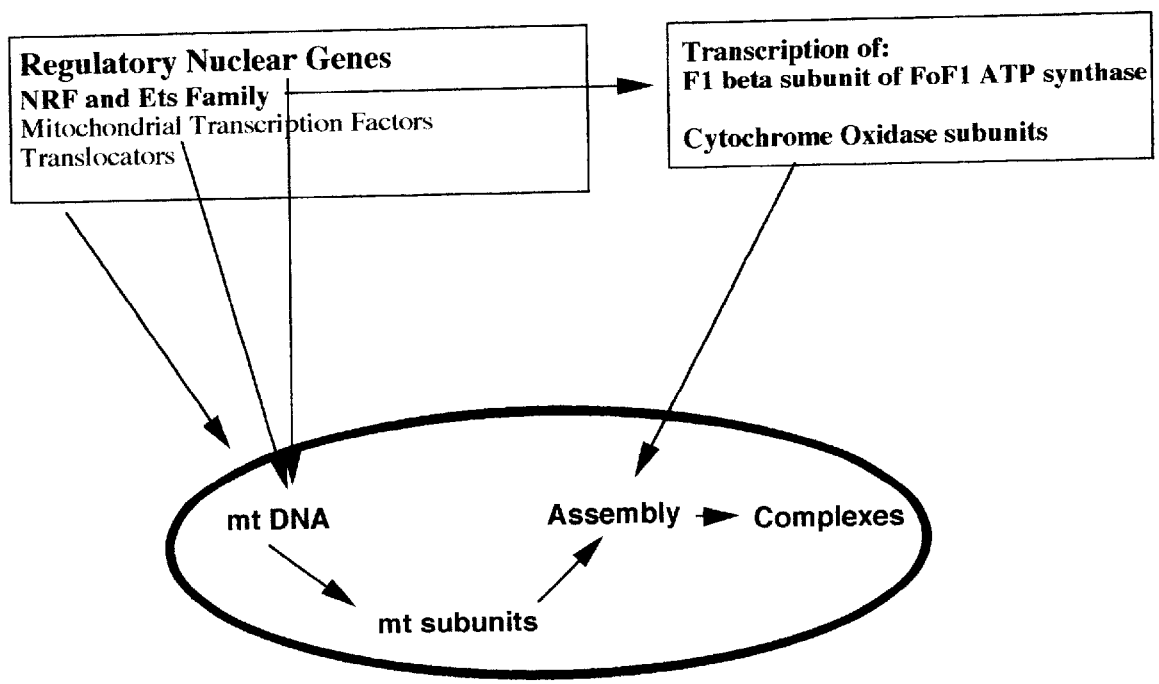
FIG. 3 shows the regulation of mitochondrial complex expression.

The subunits not encoded by the mitochondrial DNA are encoded by nuclear DNA. Nuclear DNA also encodes for protein factors controlling mitochondnal transcription, translation and coordinated expression of nuclear and mitochondrial gene expression[26]. However, as opposed to nuclear encoded gene expression, mitochondrial subunits may be regulated by the changes in mitochondrial DNA copy number[27]. The human[28] and rat[29] genome have been cloned and sequenced and there is a great deal of homology between mammalian species. Finally. the substrates for these enzymes, namely adenine, phosphates[30] and pyruvate[31] are transported into the mitochondria by nuclear encoded substrate translocators residing in the inner mitochondrial membrane. These interactions are summarized in FIG. 3.

EXAMPLE 1

Animal Studies

Protein-energy deprivation influences mitochondrial function in muscle. These effects can be directly measured in muscle by measuring the electron chain transfer activity in muscle mitochondria, and accordingly, is within the scope of the present invention. However, in human studies repeated muscle biopsies are unlikely to be used in routine clinical practice. Therefore, the effect of nutrition on the mitochondria of another cell, namely the lymphocyte was compared to the changes in muscle mitochondria. The lymphocyte is preferable, because nutrition reduces immune function and is therefore likely to have an effect on lymphocytes. Second, lymphocytes can be easily obtained by taking a blood sample. Third, lymphocytes can be separated from blood as a purified fraction. In order to substantiate the ability of mitochondrial complex activity in muscle and lymphocytes to respond to the nutritional status, the activity of mitochondrial complexes in muscle and lymphocytes of rats fed hypocalorically (reduced energy intake in relationship to requirements resulting in weight loss) was compared with controls. In addition, the effect of refeeding protein without nonprotein energy to hypocalorically fed rats was examined. In order to control intake precisely, enteral feeding through a gastrostomy was used in the studies.

Materials and Methods

Animals and Protocol:

Male Wistar rats (Charles River Canada, Inc, Quebec, Canada) were housed in individual cages in a temperature-controlled room (22° C.) with a 12-hour light:dark cycle. On entry to the animal facility, rats weighed 200–220 g. They had free access to rat chow (Purina is rodent chow 5001, Ralston Purina comp., Strathroy, Canada) for 6 days and then the enteral feeding catheter was inserted and they were fed a liquid formula diet as described below.

Diet

The composition of the different liquid defined formula diets. All the diets provided comparable amounts of electrolytes, fluid, trace elements and vitamins in sufficient quantities to meet the requirements for rats. The controls in addition received sufficient calories and protein to grow normally. The hypocaloric animals were fed a diet deficient only in protein and calories but received the same amount of fluid, electrolytes, trace elements and vitamins as the controls. Therefore, our experiments demonstrated purely the effect of protein-calorie malnutrition without being confounded by the deficiency of electrolytes, trace elements and vitamins.

Experimental Design

During the study, the animals were housed individually in metabolic cages, and catheter and spring were connected to a swivel, allowing the rats to move freely. They were randomly allocated to the following groups.

CG (control group; n=11): received enterally control diet at the rate 2.5 mL/h, resulting in the infusion of 60 mL containing 363 KJ/24h, for 7 days.

HG (hypocaloric group; n=11): received enterally hypocaloric diet at the same rate as control. resulting in the infusion of 60 mL containing 91 KJ/24h, for 7 days.

In order to demonstrate the early effects of protein refeeding in animals previously malnourished by hypocaloric feeding we studied a group of animals as indicated below:

HPRG (hypocaloric protein refeeding group; n=11): received enterally hypocaloric diet for 7 days then hypocaloric diet containing the same total protein intake as the controls for 1 day at the same rate as control, resulting in the infusion of 60 mL containing 91 then 128 KJ/24h.

In order to observe the effect of refeeding "empty calories" without protein in animals previously malnourished by hypocaloric feeding we studied another group as given below:

HGRG (hypocaloric glucose refeeding group; n=11): received enterally hypocaloric diet for 7 days then hypocatoric glucose supplemented diet for 1 day at the same rate as control, resulting in the infusion of 60 mL containing 91 then 128 KJ/24h.

In these two groups HPRG and HGRG, the total energy (from protein and non-protein sources) intake was increased by 40% as compared with the time when they were receiving hypocaloric feeding. The difference between HPRG and HGRG was the fact that the increased energy was supplied as protein in the former and as glucose in the latter.

All of the animals were observed carefully, weighed daily and allowed to take water freely throughout the experiment. The liquid defined formula diets were administered continuously for 7 or 8 days, at a constant rate, using Harvard infusion pump (Pump 22; Harvard Apparatus, Wellesley, Mass.).

Blood and Muscle Analysis

After 7 days of diet treatment, the rats were anaesthetized with pentobarbital. Six mL of blood were drawn by cardiac puncture and put into Leuco-prep$^R$ tube (Becton Dickinson Canada Inc) for mononuclear cell isolation. Soleus and gastrocnemius were removed and storaged on ice until they were processed for mitochondrial isolation.

Isolation of Muscle Mitochondria

The soleus and gastrocnemius muscles were trimmed of fat and connective tissues, chopped finely with a pair of scissors for mitochondrial isolation.

The muscle fraction was rinsed in ice-cold medium A (120 mmol/L KCI, 20mmol/L Hepes, 2 mmol/L $MgCl_2$, 1 mmol/L EGTA, 5 g/L BSA, pH 7.4) to removed any blood. The disrupted muscle is made up to 20 vol with respect to the original wet weight of tissue with medium A and homogenized with a hand- held Tefloniglass homogenizer (tenbroeck tissue grinders, Wheaton, VWR Canlab, Mississauga, Canada). The homogenate is centrifuged at 2,200 rpm for 10 min. The pellet is resuspended in 8 vol of medium A and centrifuged (2,200 rpm for 10 min). The second supematant is combined with the first. The combined supernatants are centrifuged (12,000 rpm for 10 min), and the pellets containing the mitochondria are resuspended in 10 vol of medium A and then centrifuged at 7,500 rpm for 10 min. The pellets are resuspended in 10 vol of medium B (300 mmol/L sucrose, 2 mmol/L Hepes, 0,1 mmol/L EGTA, pH 7.4) and centrifuged (5,500 rpm for 10 min), and the mitochondrial fraction is finally suspended in a small volume of medium B (approx. 5 mg/mL) and weighted. The samples are stored at −70 C.

Isolation of Lymphocytes

Briefly, the blood tubes were stored upright at room temperature for 90 min and they were centrifuged for 20 min at 3,700 rpm at room temperature. The lymphocytes layer was transferred to a 15 mL conical tube and made up to 10 mL with phosphate buffer saline (PBS, 20 mmol/L, pH 7.5). The cells remaining in Leuco-prep$^R$ were washed with PBS. The tubes were centrifuged for 15 min at 1,600 rpm at room temperature, The lymphocytes layer was isolated and resuspend by gently vortexing and PBS was added to bring volume to 10 mL and centrifuged for 10 min at 1,600 rpm at room temperature. The supernatant was discarded and the fresh cell pellet was stored on ice.

Isolation of Lymphocyte Mitochondria[32]

Fresh cell pellets were sonicated for 15 s (three bursts of 5 s each) at 30 W on ice in a medium consisting of 0.5 mL of 0.3 mol/L sucrose, 1 mmol/L EDTA, 5 mmol/L MOPS, 5 mmol/L $KH_2PO_4$ buffer pH 7.4. Then, the same buffer was added up to a final volume of 2 mL. And centrifuged at 5 C for 10 min at 2,500 rpm. The supernatant was decanted and centrifuged for 10 min at 12,000 rpm at 5 C. Afterwards, the supernatant was discarded and the pellet was suspended in 200 L of PBS (20 mmol/L. pH 7.2) and stored at −70 C.

Enzyme Assays

Protein concentrations for lymphocytes and muscle mitochondria fractions and for homogenate muscle were determined according to Lowry et al.[33]

The lymphocyte mitochondria were adjusted with PES (20 mmol/L, pH 7.2) to a protein concentration of 5 g/L. The muscle mitochondria to be assayed for Complexes I and II were diluted with PBS (20 mmol/L, pH 7.2) to a protein concentration of 1.2 g/L. Similarly, the muscle muscle mitochondria to be assayed for Complexes III and IV were diluted with medium B to a protein concentration of 1.2 g/L. The samples were frozen and thawed three times to disrupt the mitochondrial membrane for measurement of citrate synthase, Complex I and Complex II activities.

Citrate Synthase (EC 4.1.3.7) was measured in the homogenate muscle, in the lymphocytes and muscle mitochondria fractions. Briefly. the method is based on the chemical coupling of CoASH released from acetyl CoA during the synthesis of citrate, to Ellman's reagent, 5,5' dithiobis-(2-nitrobenzoic acid) (DTNB), The reaction mixture was 0.96 mL of Tris-HCI buffer (0.1 mol/L, pH 8), 20 L of DTNB (10 mmol/L in Tris-HCl buffer), 5 or 10 µL of homogenate (25 to 50 g protein) and 10 µL of potassium oxaloacetate (50 mmol/L, pH 7.5). The reaction was carried out at 25° C. and followed at 412 nm with 530 nm as a reference in a double-beam instrument (spectrophotometer DU Series 600, Beckman Instruments, Fullerton, Calif.). Most mitochondrial preparations contain acetyl-CoA hydrolase activity so this activity must be determined first for final calculations of citrate synthase activity.

Complex I (NADH:CoenzymeQ oxydoreductase) was measured by following the decrease in absorbance due to the oxidation of NADH at 340 nm as the rotenone-sensitive NADH-Ubiquinone oxidoreductase activity. Briefly, mitochondria were added to buffer containing 25 mmol/L PBS (pH 7.2), 5 mmol/L $MgCl_2$, 2 mmol/L KCN. 2.5 g/L bovine serum albumin (fraction V), 2 mg/L antimycin A, 0.13 mmol/L NADH, and 65 µmol/L ubiquinone. The NADH ubiquinone oxydoreductase activity+any non-specific change was measured for 4 min. Then 2 mg/L rotenone was added to inhibit Complex I and the resulting non-specific activity was was measured for an additional 3 min and subtracted from the total activity.

Complex II ($CoenzymeQH_2$-Cytochrome c reductase) was measured by following the reduction of 2,6-dichlorophenolindiphenol at 600 nm. Briefly, mitochondra were preincubated in buffer containing 25 mmol/L PBS (pH 7.2), 5 mmol/L $MgCl_2$, 20 mmol/L succinate at 30° C. for 10 min. antimycin A (2 mg/L), 2 mg/L rotenone, 2 mg/L KCN, and 50 µmol/L dichlorophenolindophenol were added and a baseline rate was recorded for 3 min. The reaction was started with ubiquinone (65 µmol/L) and the enzyme activity was measured for 4 min.

Complex III (SuccinateCoenzymeQ-Ferricytochrome c reductase) was measured by monitoring the reduction of cytochrome c at 550 nm with 580 nm as the reference wavelength[34]. Briefly, mitochondria were preincubated at room temperature in a buffer containing 50 mmol/L PBS (pH 8), 0.1 mmol/L EDTA, 2 g/L defatted bovine serum albumin, 3 mmol/L sodium azide, 60 µmol/L ferricytochrome c for 3 min. The reaction was started with 0.1 mmol/L decylubiquinol and the enzyme activity was measured for 4 min. The nonenzymatic rate was measured in the same conditions after addition of 10 mg/L antimycin A.

Complex IV (Cytochrome c oxidase) was the terminal member of the respiratory chain and catalized the transfer of 4 electrons from ferrocytoch rome c to molecular oxygen, with the simultaneous pumping of protons across the mitochondrial inner membrane from the matrix to the cytoplasmic side[35]. Briefly, mitochondria (0.5 to 5 g/L) were preincubated in ice in a buffer containing 100 mmol/L PBS (pH 7.2), 25 mmol/L sodium chloride, and 15 g/L dodecymaltoside for 5 min. The reaction buffer contained 50 mmol/L PBS (pH 7.2), 1 mmol/L of dodecymaftoside, and 10 µL of mitochondria preincubated mixture. The reaction was started by addition of 15 µmol/L of ferrocytochrome c (oxidised form) and the apparent first-order rate constant, k, was determined after fully oxidizing cytochrome c by addition of potassium ferricyanide at 550 nm with 580 as the reference wavelength.

Eessin Of The Results And Statistical Analsis

Muscle Results

Complex I, II, and III activities were expressed as nmole/min/mg protein and Complex IV activity as $min^{-1}$ mg protein-$^{-1}$. Citrate synthase activity in total muscle and in mitochondrial suspension were expressed as nmole/min/mg protein. The concentration of enzyme activity in the mitochondrial fraction as compared with the homogenate was determined by the ratio of citrate synthase activity in mitochondria fraction and total muscle.

Lymphocyte Results

Because of the small weight of lymphocytes obtained after purification, only Complex I and citrate synthase activities were measured in the mitochondrial suspension and expressed as nmol/min/mg protein.

Statistical Analysis eAl results were presented as means±SD. The differences between CG, HG, HNPG, and HGG groups were tested by analysis of variance (ANOVA) for statistical significance. If the ANOVA was significant ($P<0.05$), the differences between group means were tested by the Newman-Keuls test. The nonparametric Wilcoxon test and Mann-Whitney test were used to compared the absolute weight or weight change for each group and between the 4 groups. The Spearman correlation was used for correlations.

Results

Body Weight

Body weights showed no significant difference in all groups on the day of surgery and just prior to starting the diets (7 days after surgery). In CG (control) rats feeding the formula diet resulted in significant weight gain. The weight of CG rats increased from 246.1±16.0 to 293.4+18.2 g (P<0.01), corresponding to a gain of 2.7±0.5% of body weight per day. By contrast during hypocaioric feeding the weight of HG. HPRG and HGRG rats decreased from 250.2±14.3 to 204.2±15.21 g (P<0.01), 256.5±12.2 to 212.6±8.1 g (P<0.01), and 264.2±16.0 to 216.4±18.59 g (P<0.01), corresponding to 2.6±0.3, 2.4±0.3 and 2.6±0.6% loss of weight per day respectively. Refeeding protein for a day after hypocaloric feeding did not significantly increase body weight in HPRG at day 7. In contrast refeeding glucose alone in the HGRG resulted in a further decrease in weight (P<0.02). Feeding "empty calories" was less effective than protein in halting weight loss resulting from hypocaloric feeding, Effect of Hypocaloric Feeding and Refeeding on the Citrate Synthase Activity Citrate synthase is a marker enzyme of the mitochondrial matrix. The activity of this enzyme is an index of the mass of mitochondrial matrix present in the sample Muscle There was no significant difference in the citrate synthase activity in the homogenates of soleus (P=0.54) and gastrocnemius (P=0.22) between the CG, HG, HPRG and HGRG rats. Moreover, there was no significant difference in the citrate synthase activity in the mitochondrial fraction of soleus (P=0.33) and gastrocnemius (P=0.17) between CG, HG. HPRG and HGRG rats. The concentration of enzyme activity in the mitochondrial fraction as compared with the homogenate was not significantly different in the soleus (P=0.55) and gastrocnemius (P=0.40) between CG, HG, HPRG and HGRG rats.

Lymphocyte

The citrate synthase activity in the lymphocyte mitochondrial fraction was significantly higher in HGRG than in CG (17.5±6.7 vs 12.3±3.0 nmol/min/mg protein. P<0.04) and than HPRG (17.5±6.7 vs 11.98±2.82 nmol/min/mg protein, P<0.05). There was no significant difference between CG, HG and HPRG rats (12.33±2.99 vs 13.47±4.83 vs 11.98±2.82 nmol/min/mg protein).

Since the activity of this enzyme was not influenced by malnutrition, it was used as a reference for mitochondria.

Effect of Hypocaloric Feeding on Complexes I, II, III and IV Active

Muscle

Figure 4:
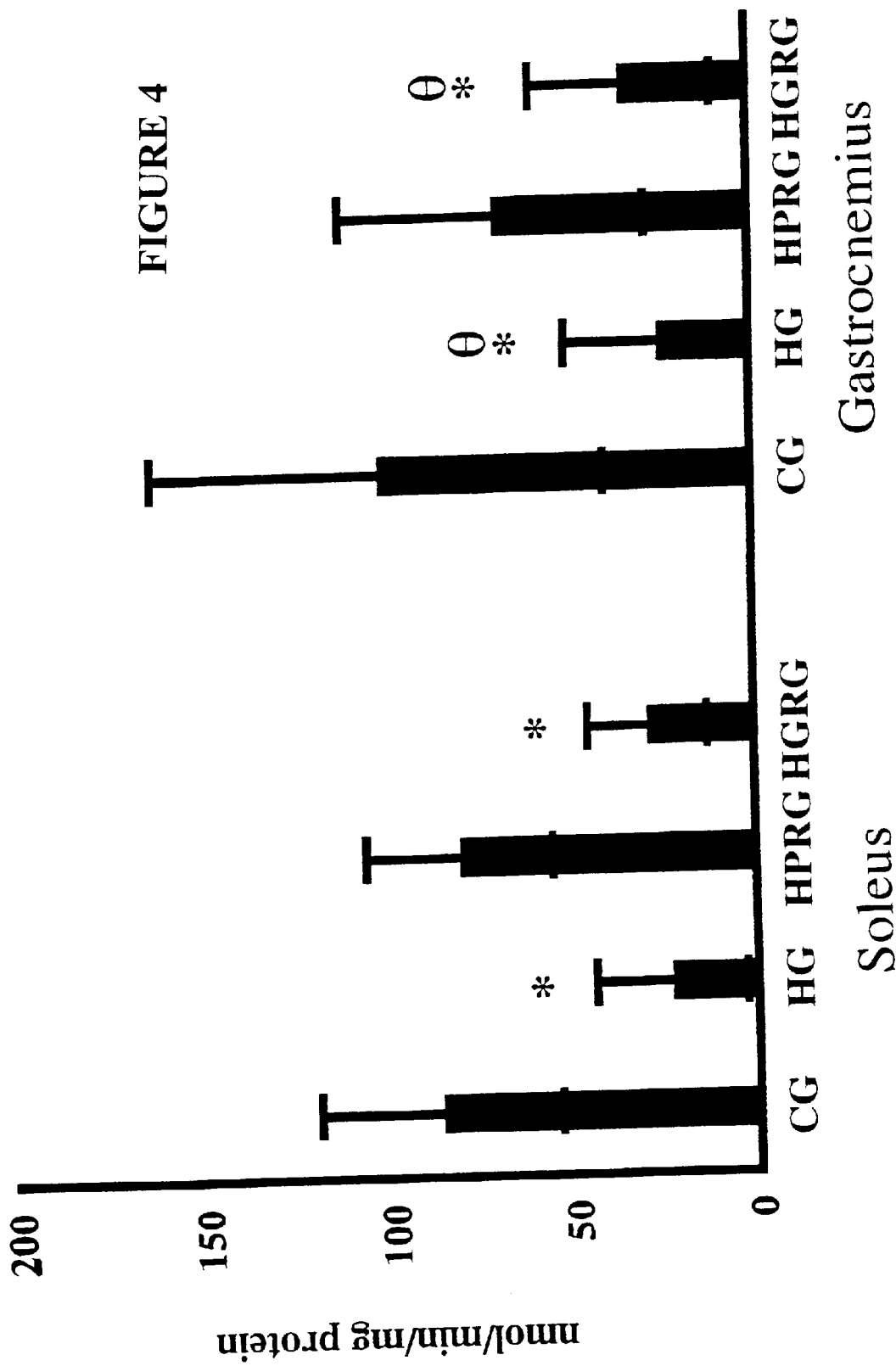
FIG. 4 is a bar graph showing Complex I activity in soleus and gatrocnemius of control (CG), hypocaloric (HG), hypocaloric protein refeeding (HFPRG) and hypocaloric glucose refeeding (HGRG) groups(n=11 rats/group) (*P<0.01 vsCG and HPRG for soleus, by ANOVA and Newman-Keuls test)
Figure 5:
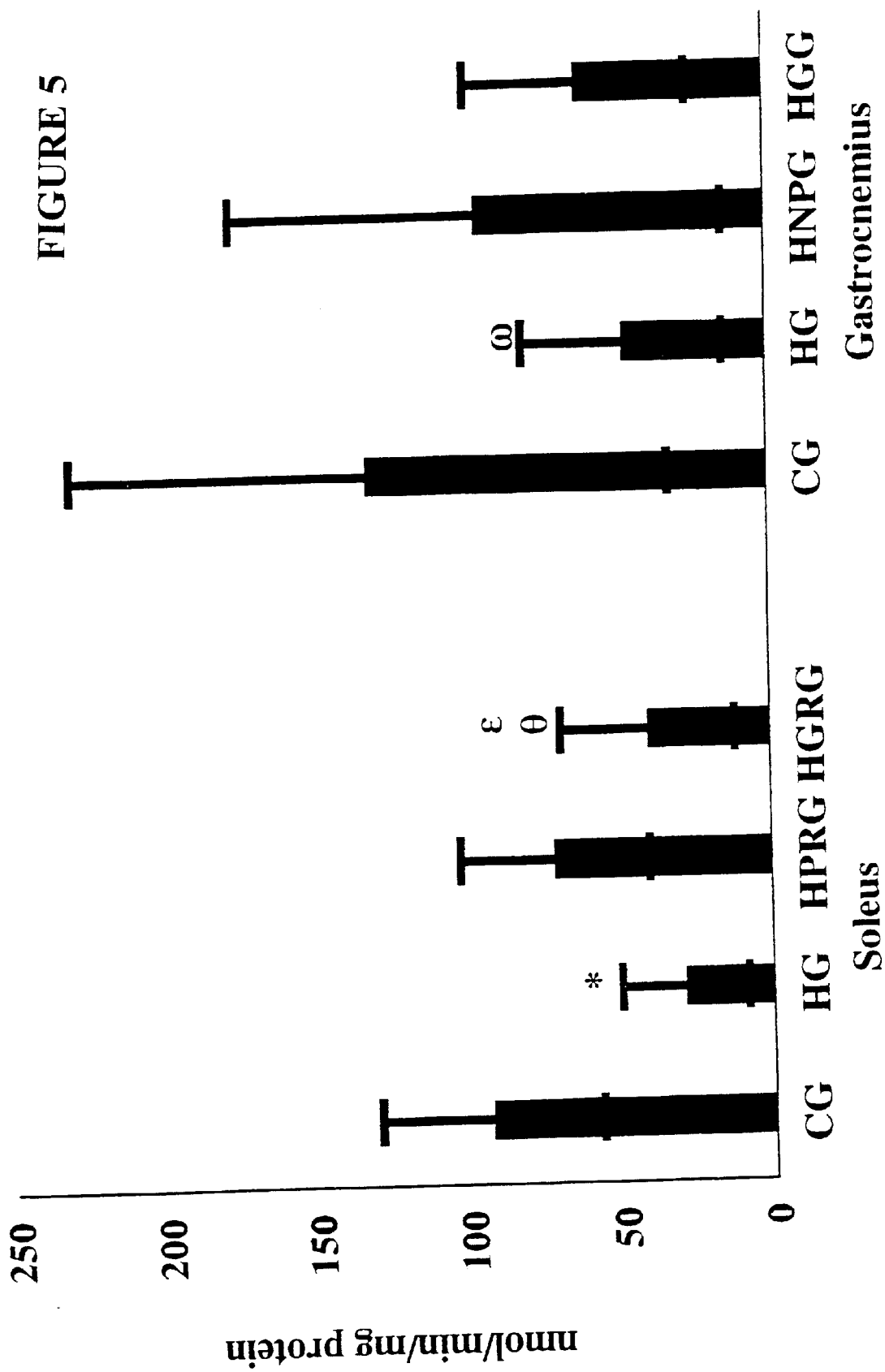
FIG. 5 is a bar graph showing Complex II activity in soleus and gatrocnemius of control (CG), hypocaloric (HG), hypocaloric protein refeeding (HPRG) and hypocaloric glucose refeeding (HGRG) groups, (n=11 ratsgroup). (*P<0.01 vs CG and HPRG. e P<0.01 vs CG, q P<0.02 vs HPRG for soleus, by ANOVA and Newman-Keuls test)
Figure 6:
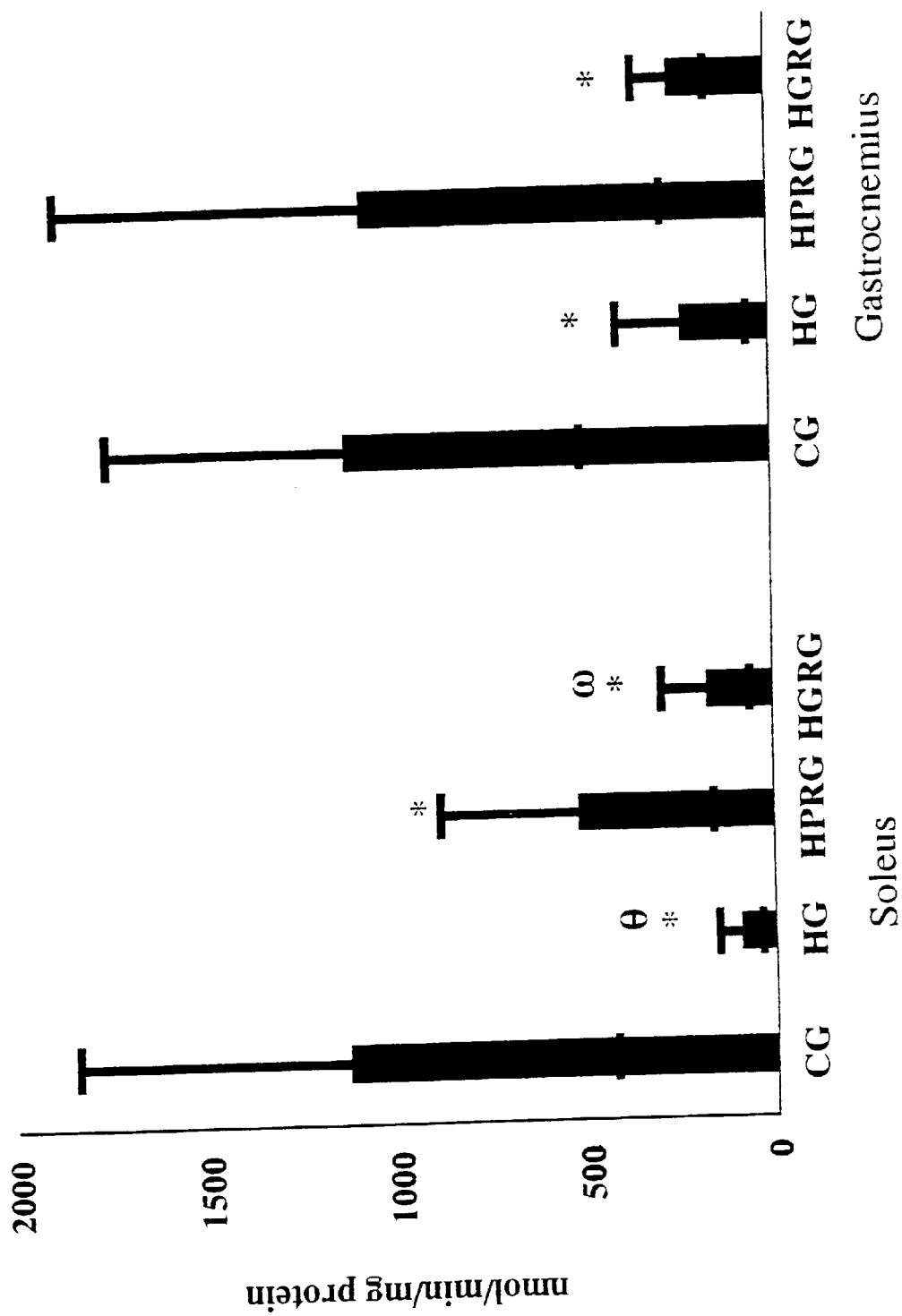
FIG. 6 is a bar graph showing Complex III activity in soleus and gatrocnemius of control (CG), hypocaloric (HG), hypocaloric protein (HPRG) and hypocaloric glucose refeeding (HGRG) groups,(n=11 rats/group) (*P<0.01 vs CG, q P<0.02 vs HPRG and w P<0.05 vs HPRG for soieus, by ANOVA and Newman-Keuls test)
Figure 7:
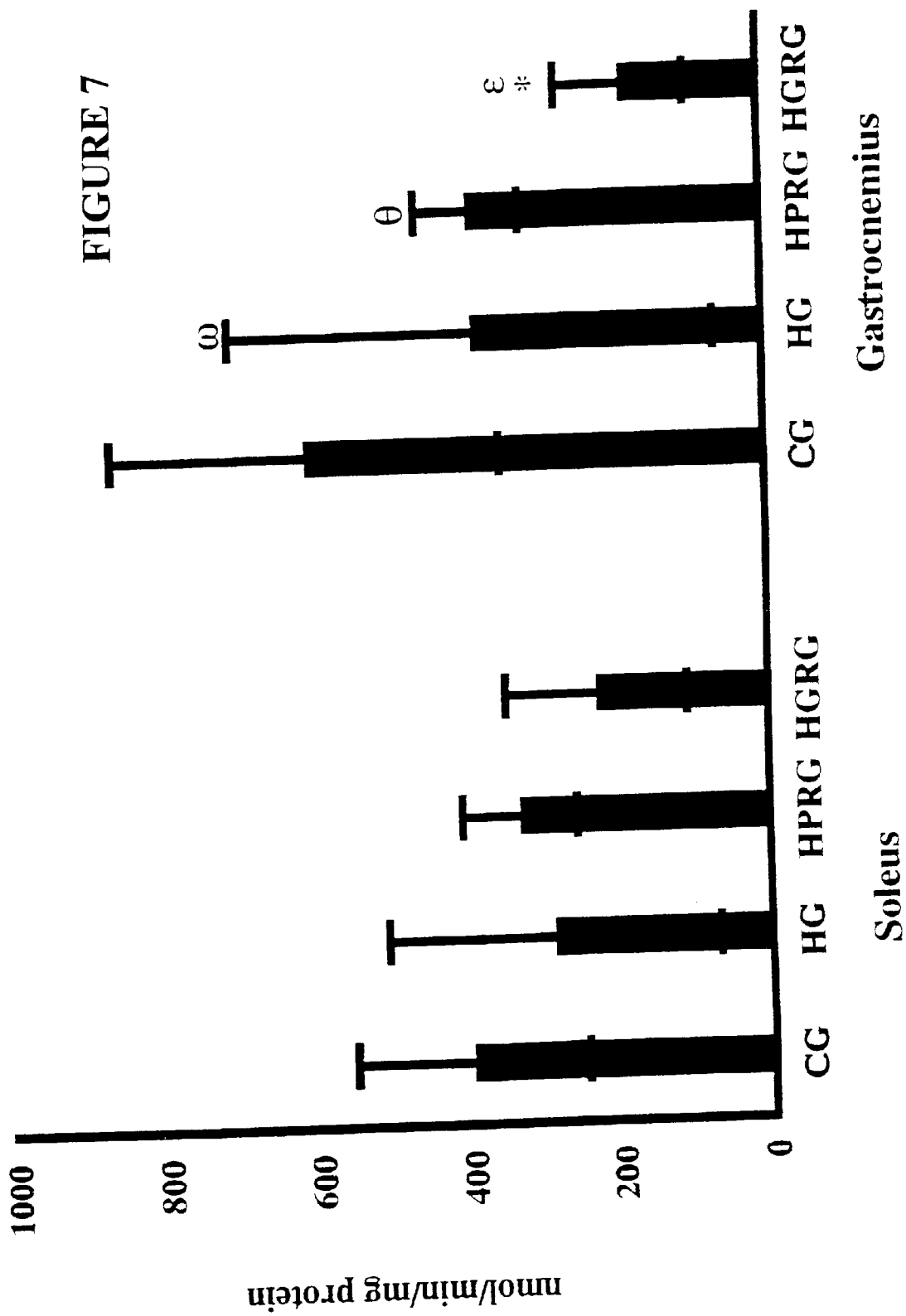
FIG. 7 is a bar graph showing Complex IV activity in soleus and gatrocnemius of control (CG), hypocaloric (HG), hypocaloric protein refeeding (HPRG) and hypocaloric glucose refeeding (HGRG) groups,(n=11 ratstgroup)

As shown in FIGS. 4–6, there was a significant decrease of Complexes I, II and III in soleus (−73%, −68%, and −92% respectively) and in gastrocnemius (−75%, −64%, and−79% respectively) between the CG and the HG rats. As shown in FIG. 7, Complex IV was significantly decreased in gastrocnemius (−37%) and not significantly different in soleus (−28%) between the CG and the HG.

Figure 8:
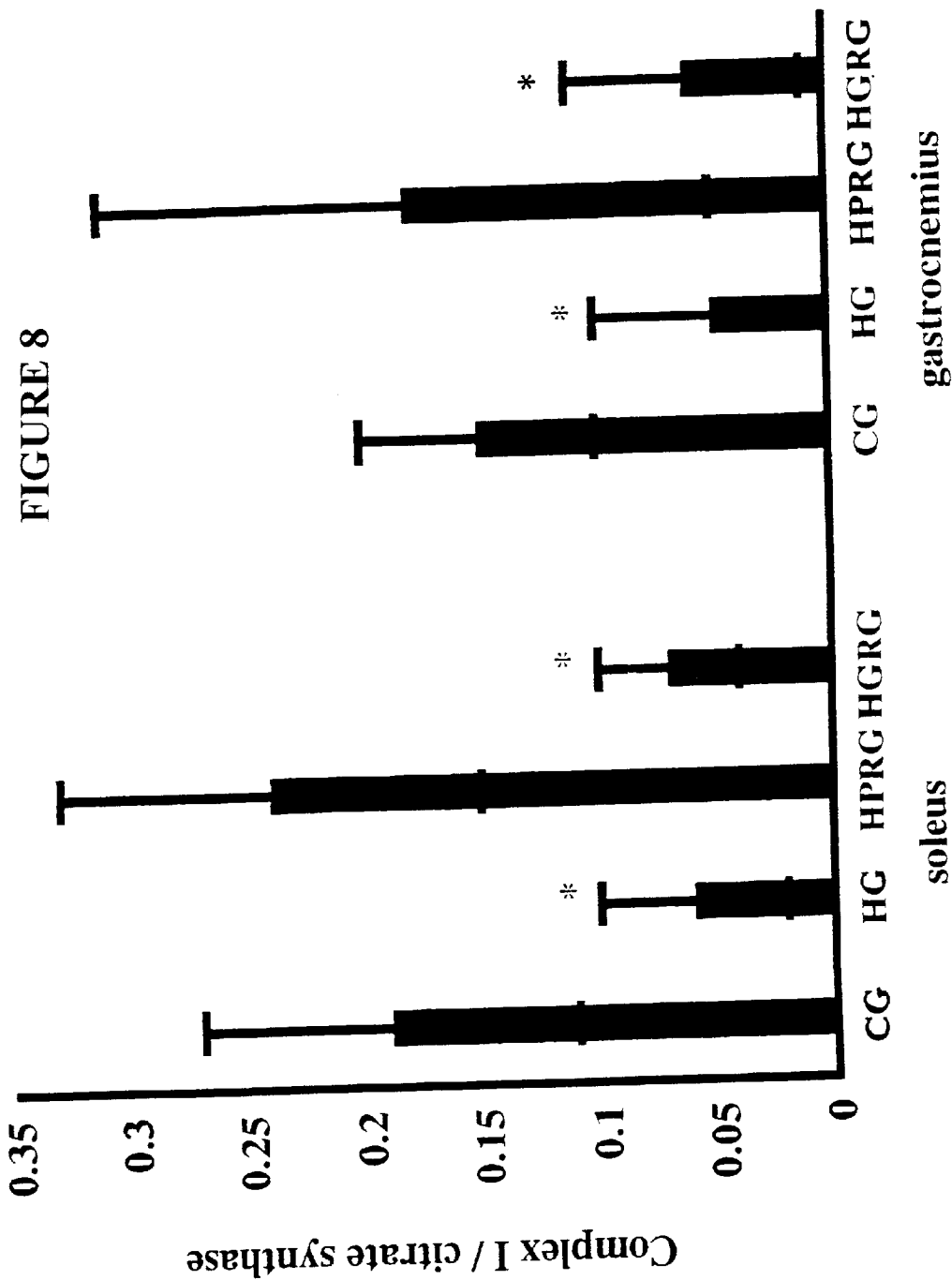
FIG. 8 is a bar graph showing the ratio of Complex I to citrate synthase activity and Complex IV in soleus in control (CG), hypocaioric (HG), hypocaloric protein refeeding (HPRG) and hypocaloric glucose refeeding (HGRG) groups, (n=11 rats/group) (*P<0.01 vs CG and HPRG for soleus) (+P<0.01 vs HG, by ANOVA and Newman-Keuls test)
Figure 9:
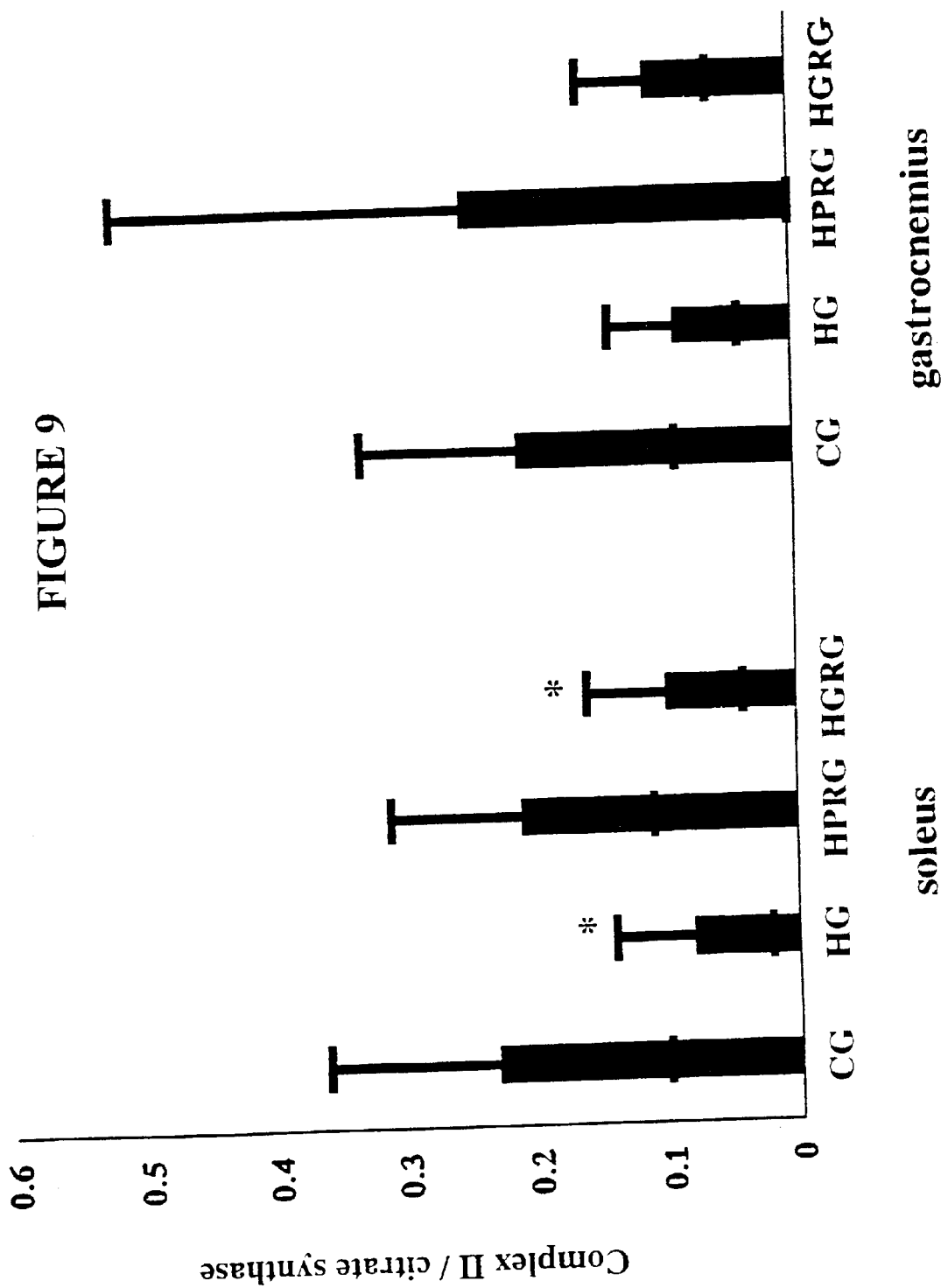
FIG. 9 is a bar graph showing ratio of Complex It to citrate synthase activity and Complex IV in soleus in control (CG), hypocaloric (HG), hypocaloric protein refeeding (HPRG) and hypocaloric glucose refeeding (HGRG) groups, (n=11 rats/group) (*P<0.01 vs CG and HNPG) (+P<0.01 vs HG, by ANOVA and Newman-Keuls test)
Figure 10:
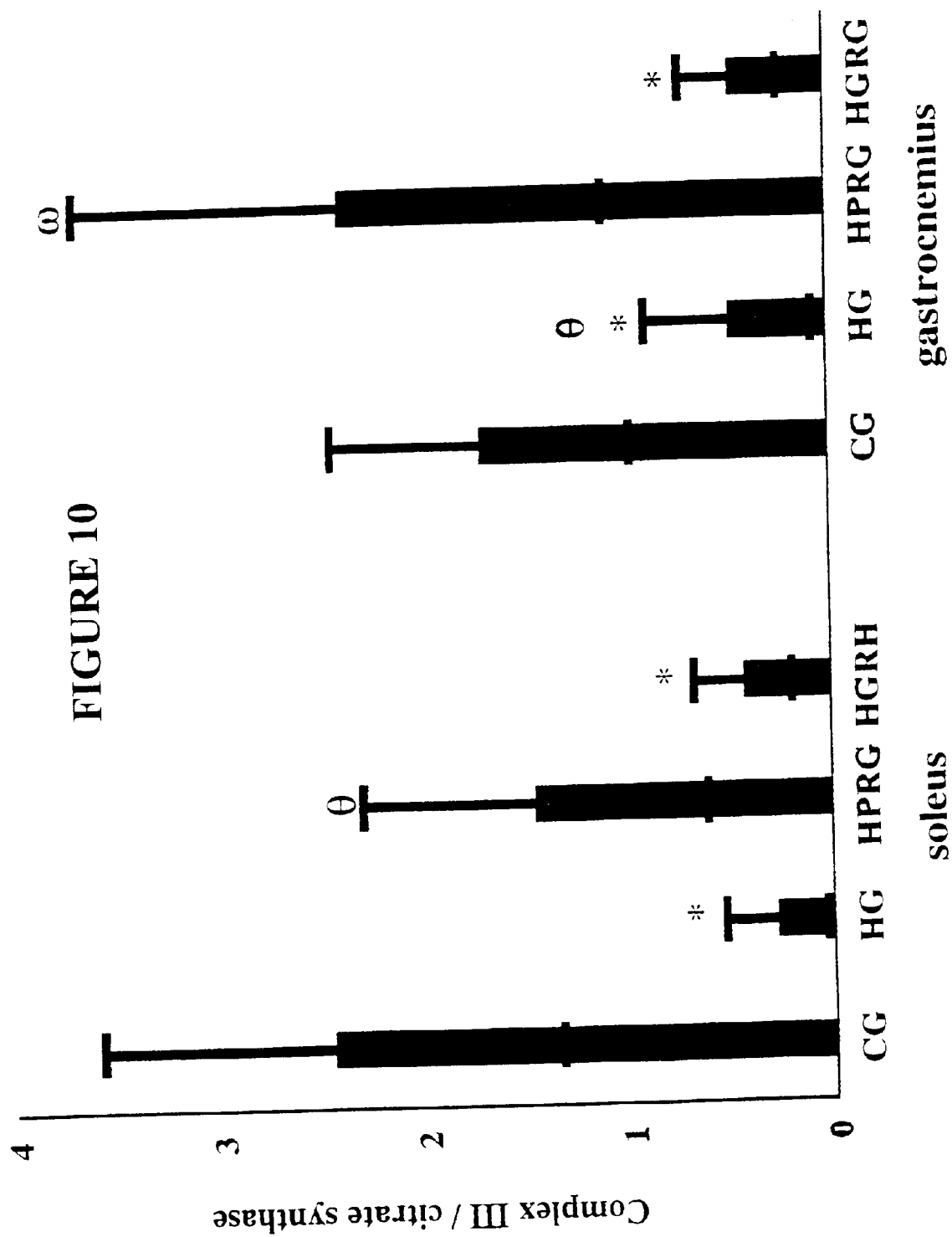
FIG. 10 is a bar graph showing the ratio of Complex III to citrate synthase activity and Complex IV in soleus in control (CG), hypocaloric (HG), hypocaloric protein refeeding (HPRG) and hypocaloric glucose refeeding (HGRG) groups, (n 32 11 rats/group) (*P<0.01 vs CG and HNPG and q P<0.01 vs CG in soleus) (+P<0.01 vs HG, by ANOVA and Newman-Keuls test)
Figure 11:
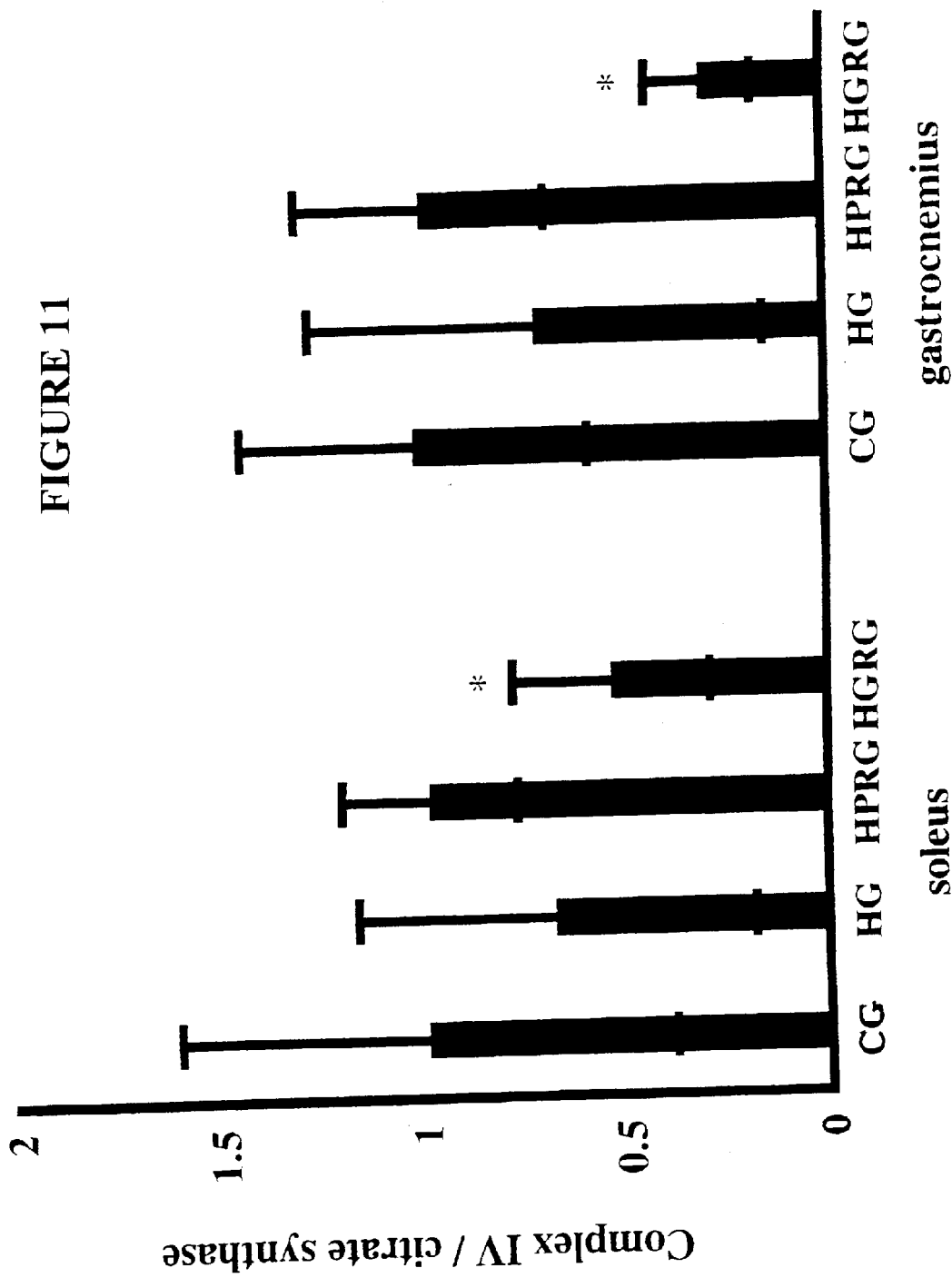
FIG. 11 is a bar graph showing ratio of Complex IV to citrate synthase activity in soleus in control (CG), hypocaloric (HG), hypocalonc protein refeeding (HPPG) and hypocaloric glucose refeeding (HGRG) groups, (n=11 rats/group); (*P<0.01 vs HPRG in soleus, by ANOVA and NewmanKeuts test)

The complexes activity normalized for the amount of mitochondrial matrix by the citrate synthase activity are shown in FIGS. 8, 9, 10 and 11. The normalized values expressed as a ratio of Complex I, II, III, I, IV/citrate synthase were significantly decreased for Complexes I, II, III (see FIGS. 8–10) for soleus and Complexes I, III for gastrocnemius (FIGS. 8 and 10). The ratio for Complexes IV for soleus and II, IV for gastrocnemius was not significantly decreased by hypocaloric feeding (FIGS. 9 and 11).

Lymphocytes

Figure 12:
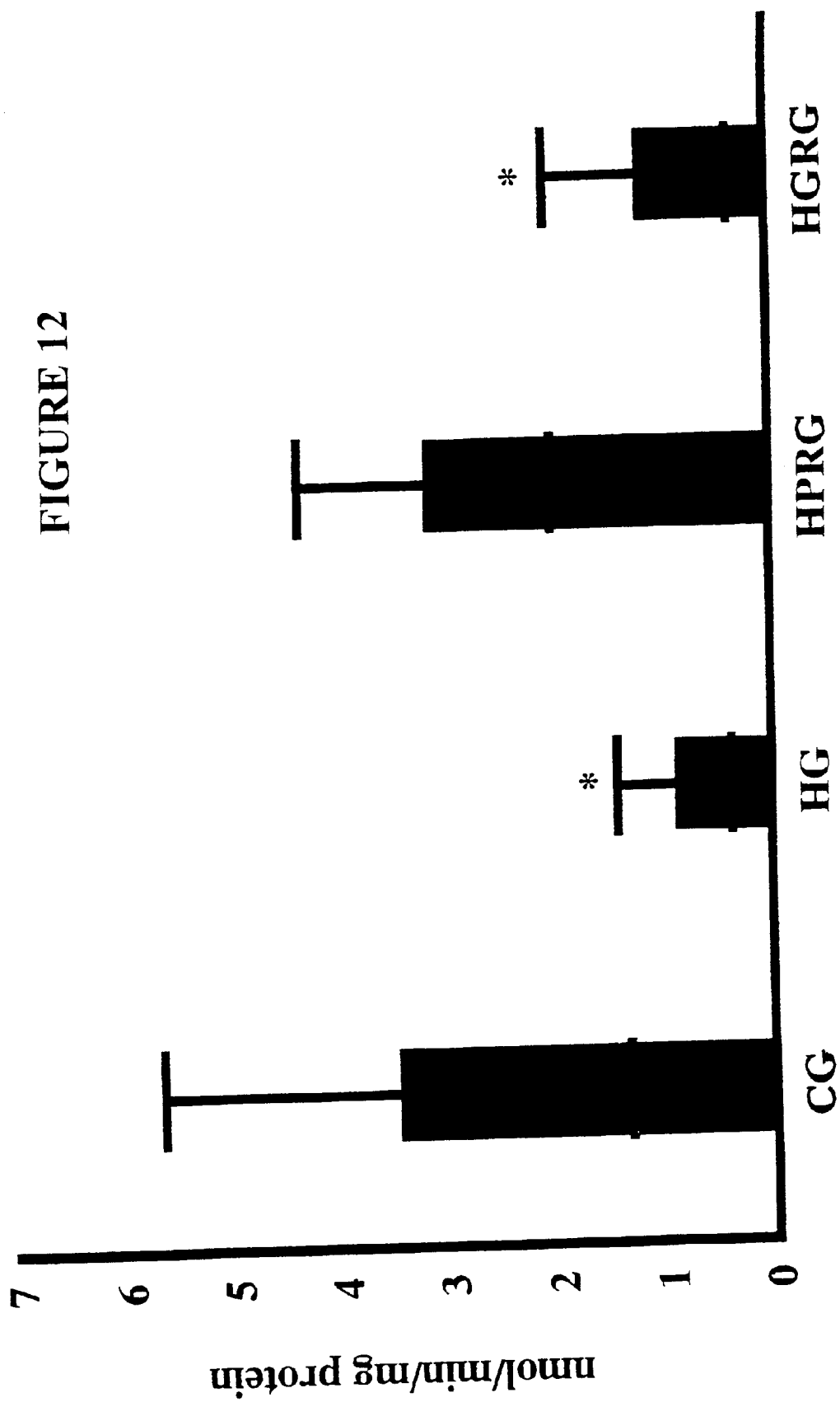
FIG. 12 is a bar graph showing Complex I activity in lymphocytes of control (CG), hypocaloric (HG), hypocaloric protein refeeding (HPRG) and hypocaloric glucose refeeding (HGRG) groups (n=11 rats/group) (P<0.01 vs CG and HPRG, by ANOVA and Newman-Keuls test)
Figure 13:
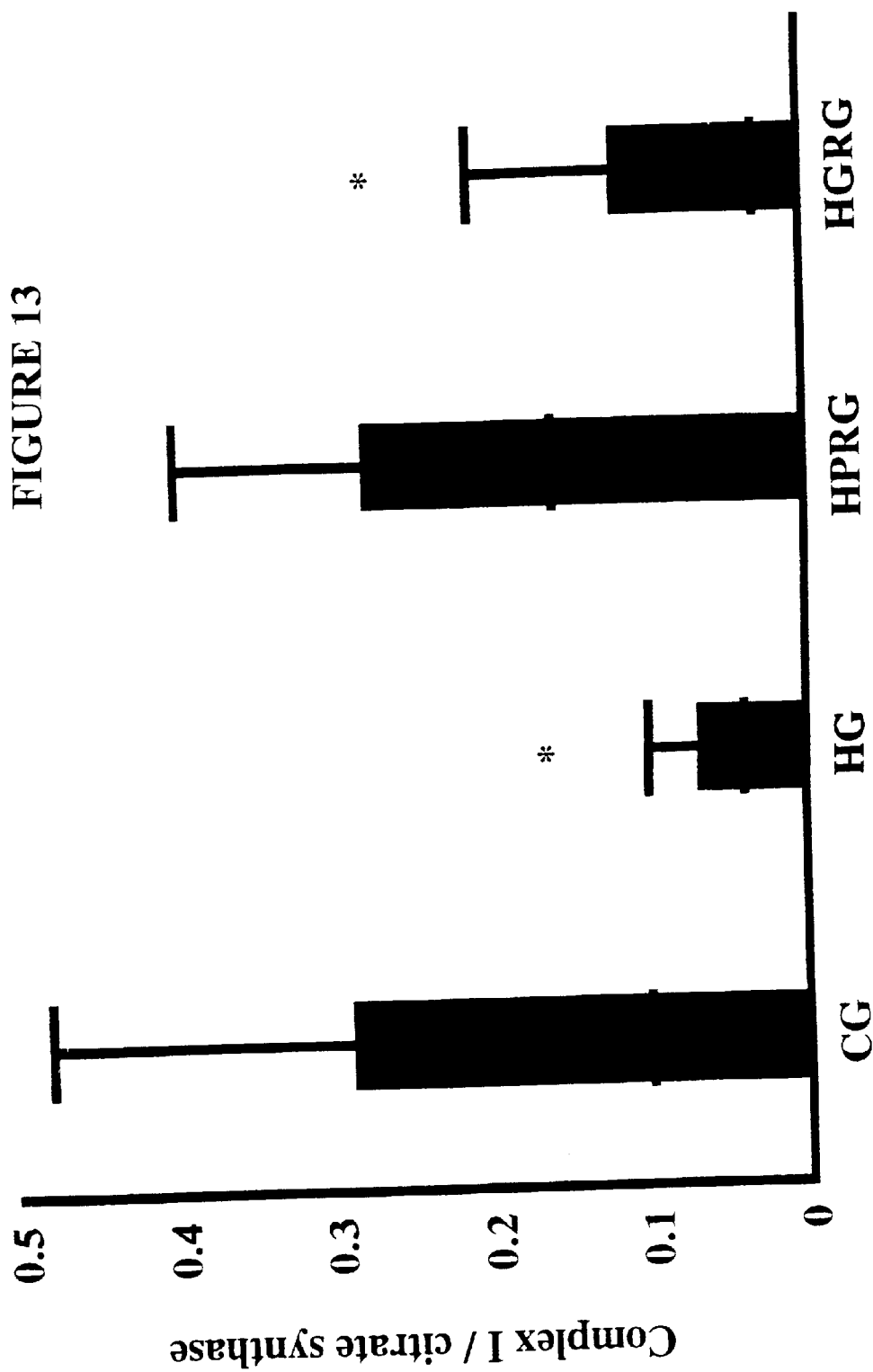
FIG. 13 is a bar graph showing Complex I activity normalyzed to the citrate synthase activity in lymphocytes of control (CG), hypocaloric (HG), hypocaloric protein refeeding (HPRG) and hypocaloric glucose refeeding (HGRG) groups (n=11 rats/group) (*P <0.01 vs CG and HPRG, by ANOVA and Newman-Keuls test)
Figure 14:
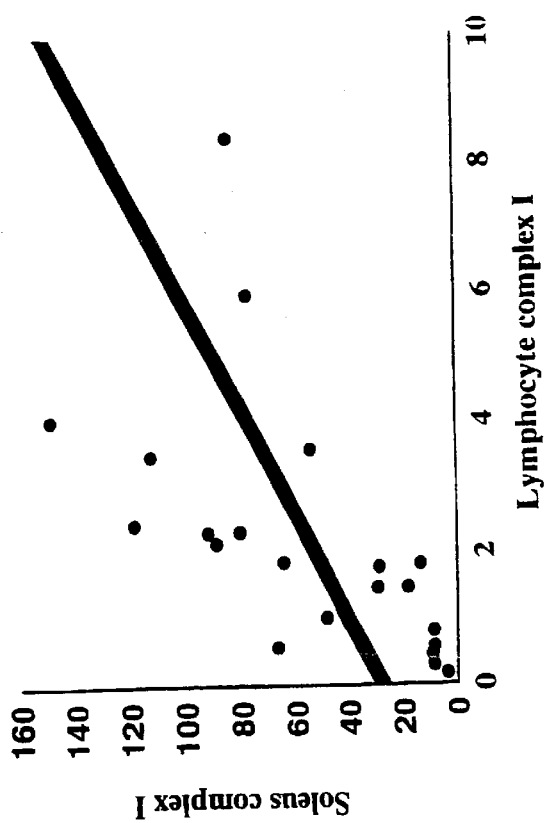
FIG. 14A shows a correlation of Complex I activity in lymphocytes with Complex I activity in the soleus muscle.
FIG. 14B shows a correlation of Complex I activity in lymphocytes with Complex I activity in the gastrocnemius muscle.
Figure 14:
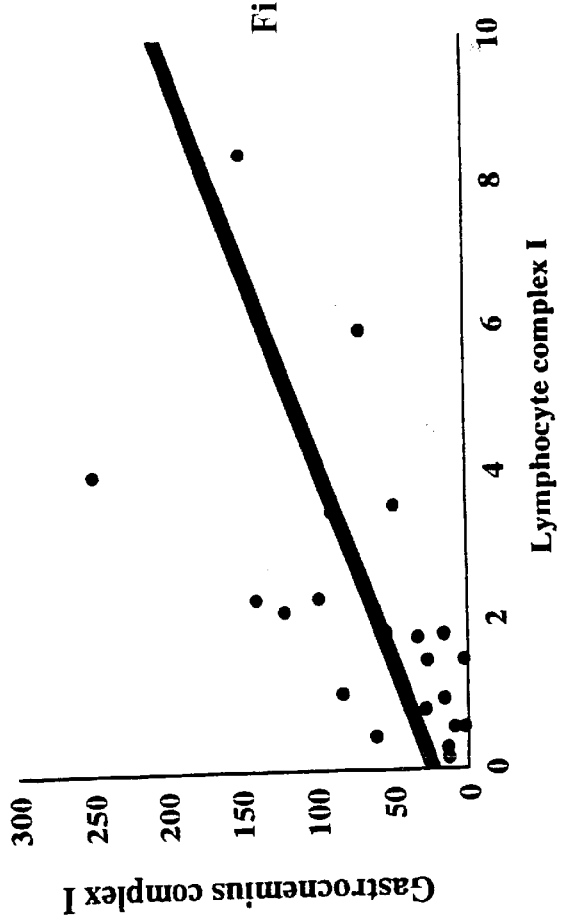
Figure 15:
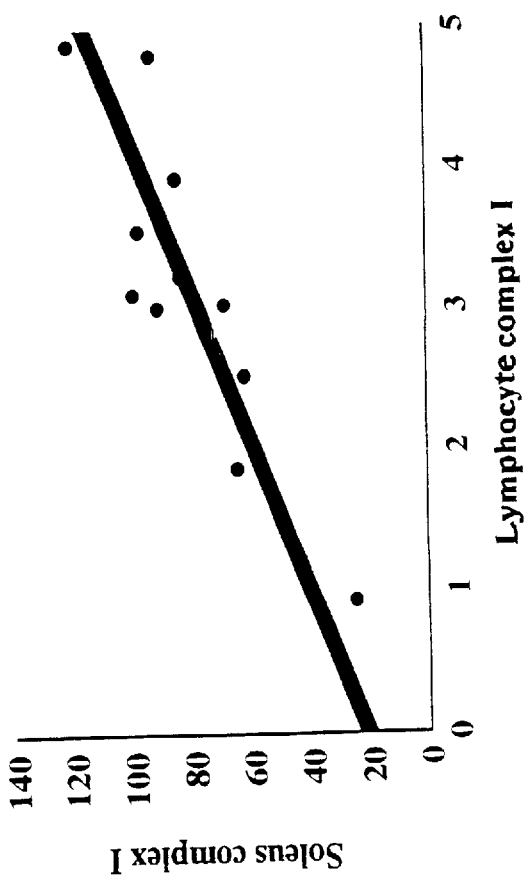
FIGS. 15A and 15B show a correlation of Complex I activity and the ratio of Complex I/Citrate Synthase in the HPRG group between lymphocytes and the soleus muscle.
Figure 15:
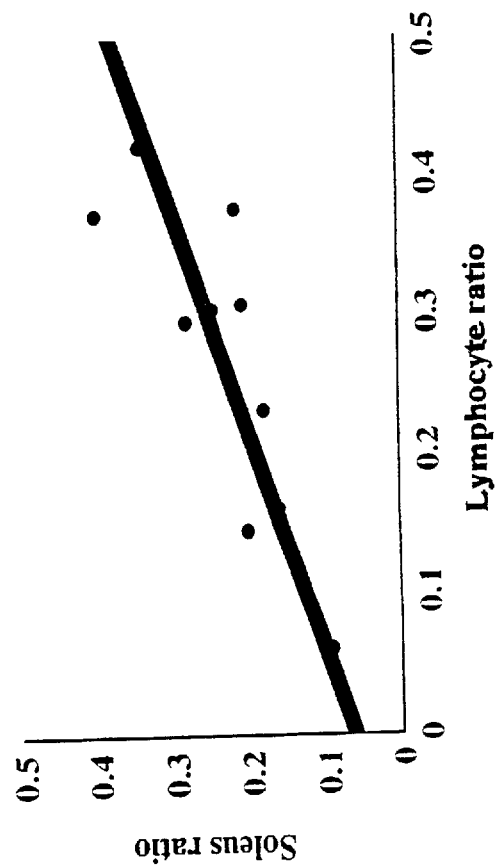

The Complex I activity in the lymphocytes mitochondrial fraction was significantly lower in HG as compared with CG rats (−74%, FIG. 12). When normalized for citrate synthase hypocaloric feeding was associated with a significant reduction of Complex I activity in lymphocytes(FIG.13).

Effect of Refeeding on Complexes I, II, III and IV Activity

Muscle

As showns in FIGS. 4–6, protein refeeding resulted in an increase of Complexes I and II in soleus and Complexes I, II, and III in gastrocnemius to the control range. However, Complex III in soleus and Complex IV in gastrocnemius remained significantly lower after protein refeeding compared to the CG (controls) (−54%, FIG. 3; and −36%. FIG. 7). Complex IV in soleus was unchanged (see FIG. 7). In contrast, refeeding glucose alone did not increase Complexes I, II, III in soleus and Complexes I and III in gastrocnemius (see FIGS. 4, 5 and 6). Complex II in gastrocnemius tended to be significanty lower after glucose refeeding compared s to the CG (p=0.057). The glucose refeeding had a negative effect on Complex IV as it tented to be significantly lower in soleus (p=0.055) and it was significantly decreased in gastrocnemius (p=0.01) when compared to the CG value, as shown in FIG. 4. Moreover, Complex IV was not significantly different between HG and HGRG in soleus but it was significantly different in gastronemius (−53%). There was significantly difference of Complexes I, II, III in soleus, Complex I, III in gastrocnemius between HGRG and HPRG (see FIGS. 1, 2 and 3). There was no significantly difference for Complex IV in soleus and gastrocnemius between HGRG and HPRG.

When the complex activity was normalyzed to the citrate synthase activity, there was a positive effect of protein refeeding in Complexes I, II, III in soleus and Complexes I, III gastrocnemius (see FIGS. 6, 7 and 8). However, Complex III activity was significantly lower in HPRG compared to CG for soleus and significantly higher in HPRG compared to CG for gastrocnemius, as best shown in FIG. 8. Protein refeeding had no effect on Complex IV activity for soleus and gastrocnemius (see FIG. 9, Glucose refeeding had no significant effect on Complexes I, II, III for soleus and Complexes I, III for gastrocnemius (see FIGS. 6, 7 and 8) because there was a significantly difference between HGRG and CG, HGRG and HPRG. Complex IV was significantly decreased after glucose refeeding in soleus and gastrocnemius when it was compared to the HPRG.

Lymphocytes

As for the soleus and gastrocnemius, only protein refeeding had a significantly effect on the Complex I activity (see FIG. 5). There was normalization for the HPRG compared to the CG rats (P=0.62). Indeed, there was no significant difference between the HG and HGRG (P=0.59) When Complex I activity was normalized to the citrate synthase, the results were comparable to the effect of protein and glucose refeeding (see FIG. 10). The ratio was also significantly decreased in HG as compared with CG rats (0.29±0.19 vs 0.07±0.03, P <0.01), while it was not different between CG and HPRG rats(0.29±0.19 vs 0.28±0.12, P=0.83) and between HG and HGRG (0.07±0.03 vs 0.12±0.09, P=0.56).

Relation between the Complexes I, II, III and IV activity in Muscle and Complex I Activity in Lymphocytes For the CG and HG groups together, the Complex I activity in lymphocytes was correlated with the Complex I activity in soleus (r=0.80, P<0.01) and in gastrocnemius (r=0.73, P<0.01) (see FIG. 11). There were also correlation with the Complexes II, III in soleus and gastrocnemius, and no correlation with the Complex IV (results not shown). Complex I normalyzed to the citrate synthase activity in lymphocytes was also correlated with the ratio in the soleus (r=0.92, P<0.01) and in the gastrocnemius (r=0.59, P<0.01). in the HPRG rats, Complex I activity in lymphocytes correlated with Complex I in the soleus (r=0.79, P<0.01) and the ratio of Complex I activity to citrate synthase in lymphocytes also correlated with the ratio in soleus (r=0.81, P<0.01) (see FIG. 12). There were no correlation for these parameters between lymphocytes and gastrocnemius. For the HGRG rats, there were no correlation for Complexes I, II, III, and IV in soleus, gastrocnemius and lymphocytes Complex I (results not shown).

Relation between Body Weight and Complexes I, II, III and IV Activity on Muscle and Lymphocytes At the time of sacrifice, Complexes I, II, III for soleus and gastrocnemius in both CG and HG rat were correlated with body weight (soleus r=0.69, r=0.76, r=0.69, gastrocnemius r=0.68, r=0.49, r=0.69, P<0.02). There was no correlation between the complexes activities in soleus, gastrocnemius and body weight at the time of sacrifice for both HPRG and HGRG rats. Complex I, II, III activities normalized to the citrate synthase activity for soleus and gastrocnemius in both CG and HG rats were correlated with the body weight in both CG and HG rats (results not shown). There was no correlation between the complexes activities normalyzed to the citrate synthase activity in soleus, gastrocnemius and body weight at the time of sacrifice for both HNGP and HGG rats. There was no correlation between Complex IV in soleus and gastrocnemius and body weight in the above two situations.

Lymphocyte Complex I activity was correlated with body weight at the time of sacrifice in CG and HG rats(r=0.81, P<0.01). Correspondingly, there was no correlation between the lymphocytes Complex I activity and body weight at the time of sacrifice in both HPRP and HGRG rats. The lymphocytes Complex I activity normalized to the citrate synthase activity was correlated with body weight at the time of sacrifice in CG and HG rats(r=073, P<0.01). Correspondingly, there was no correlation between the lymphocytes Complex I activity and body weight at the time of sacrifice in both HNGP and HGG rats.

EXAMPLE 2

Human Studies

On the basis of the above studies in rats, we hypothesised that malnutrition in humans would impair the activity of mitochondrial energetic enzymes in blood lymphocytes Methods Sixteen malnourished patients (MP, 9 Crohn's disease B7 active disease, 1 dysphagia, 4 anorexia, and 2 short bowel syndrome–7M/9F, 47±22 yrs) with at least 10% weight loss over 6 months (19±7%, range: 5–28%) and 16 healthy volunteers (HV, 4M/12F, 34±9 yrs) were recruited. After lymphocyte isolation (perroll method) and sonication, mitochondrial Complex I (C I) and citrate synthase (CS) activities were measured. In the MP group, body composition was determined using bioelectrical impedance spectroscopy (BIS) and resting energy expenditure (REE) by indirect calorimetry. Total energy intake was determined by dietary assessment and serum albumin levels were recorded, Results (means±SD. Enzymatic Activities Expressed as nmol/min/mg Protein)

In the MP group, albumin level was 27±9 g/l (range: 16–40) and the energy intake was 873±1067 kcal (range: 0–4250) or 0.8±1.1 kcal/REE (range: 0–4.4).

| | Weight(Kg) | BMI(Kg/Ht$^2$) | Citrate synthase | Complex I |
|---|---|---|---|---|
| HV | 67 ± 13 | 25.2 ± 5.2 | 41.7 ± 15.5 | 3.9 ± 1.1 |
| MP | 44 ± 8 | 16.5 ± 2.6 | 25.2 ± 20.2 | 1.9 ± 0.8 |
| P value | 0.001 | 0.001 | 0.007 | 0.001 |

Complex I ("C C I") and Citrate synthase ("CS") activities were significantly different between HV and MP. In MP, C I activity was correlated with body weight (r=0.67, P=0.03), BMI (r=0.73, P=0.001), and % weight loss (r=0.67, P=0.005). There was no correlation between C I and serum albumin, REE and energy intake. CS activity did not correlate with these parameters. Albumin did not correlate with BMI, % weight loss, and body weight. In HV group, C I did not correlate with the BMI (P=0.57) and weight (P=0.10). CONCLUSION: The results demonstrated for the first time in humans that malnutrition decreased mitochondrial enzyme activity in lymphocytes. Complex I activity was significantly affected by malnutrition and is a sensitive marker of nutritional status.

EXAMPLE 3

Human Studies

Malnutrition alters body mass and function. C I and CS activities (lymphocyte energetic function) are reduced by malnutrition. We hypothesised that refeeding would restore mitochondrial C I activity more rapidly than body mass or body composition.

Methods

Eleven mainourished patients (MP, 5 Crohn's disease, 2 cancer, 1 dysphagia 3 anorexia–5 M and 6 F, 49±17 yrs) with at least 10% weight loss over 6 months (16.4±8.0%, range: 10–28%) were recruited. Mitochondrial C I and CS activities were measured in sonicated lymphocytes isolated by the percoil method before (D0), and after refeeding (D7 and D14). Body composition was measured by bioelectrical impedance spectroscopy (BIS). Total energy intake and the serum albumin (g/l) were recorded. The mitochondria C I and CS activities were compared with previously obtained results in 16 HV (healthy volunteers, 4M and 12F, 34±9 yrs, BMI=25.2±5.2).

RESULTS (mean (SD), activities expressed as nmol/min/mg protein)

| | Weight | BMI | LBM | kcal/kg | Albumin | Complex I | Citrate S |
|---|---|---|---|---|---|---|---|
| D0 | 47.2 | 17.3 | 34.4 | 14.6 | 26 | 1.7 | 19 |
| | (10.5) | (3.6) | (8.1) | (12.3) | (7) | (0.9) | (11.3) |
| D7 | 47.3 | 17.3 | 33.7 | 30.4* | 26 | 2.6** | 29.2* |
| | (9.8) | (3.2) | (6.1) | (14.7) | (4) | (1.4) | (13.9) |
| D14 | 45.3 | 16.3 | 33.6 | 42.4* | 25 | 2.6** | 22.9*** |
| | (10.6) | (3.6) | (6.0) | (11.6) | (2) | (1.1) | (11.6) |

*P < 0.01,
**P < 0.03, and
***P = 0.02 vs D0 (Wilcoxon test).

Compared with HV (3.9±1.1), C I was significanty different at D0 (P=0.001), D7 (P=0.01) and D14 (P0.02). Change in C I (D14 vs D0) was correlated with change in energy intake (kcal/REE r=0,81, P0.015) Compared with HV (41.7 15.5). CS was significantly different at D0(P= 0.001), D7 (P=0.03) and D14 (P=0.01) There was no correlation between the changes in CS activity and energy intake (D14 vs D0).

Conclusion The results showed a rapid rise in C I activity (significant after 1 wk of refeeding) without change in the routine nutrition assessment parameters and body composition. There was a direct relationship between the change in C I activity and the improvement in energy intake. The lymphocyte C I activity may be a sensitive and rapid indicator of response to nutritional support in malnourished patients.

In mammals, protein-calorie restriction by feeding a hypocaloric diet while maintaining electrolyte, fluid, micronutrient and vitamin intake constant, reduces Complex I, II, and III activity in tissue (such as muscle and lymphocytes) comparably. Feeding protein and minimal calories restores Complex I, II, and III activity. However, feeding calories alone does not restore Complex I, II, and III activity. The lymphocytes of malnourished humans also have reduced Complex I, II, and III activity, as well as a reduction of citrate synthase activity.

It will be appreciated that the above description relates to the preferred is embodiment by way of example only. Many variations on the invention will be obvious to those knowledgeable in the field, and such obvious variations are within the scope of the invention as described and claimed, whether or not expressly described.

[1] Keys A. Brozek J, Henschel A. Mickelsen O, and Taylor H L. The Biology of Human Starvation. Vol I and II. Minneapolis, University of Minnesota Press 1950

[2] Hill G L, King R F G J, Smith R C. et al. Multielament analysis of the living body by neutron activation analysis-application to critically ill patients receiving intravenous nutrition. Br J Surg 66:868–72, 1979.

[3] Moore F D, Olesen K H, McMurrey J D, Parker H V, Ball M R, and Boyden C M. The body cell mass and its supporting environment. Philadelphia: W B Saunders 1963.

[4] Jeejeebhoy K N, J P Baker, S L Wolman, D E Wesson, B Langer, J E Harrison and K G McNeill. Critical evaluation of the role of clinical assessment and body composition studies in patients with malnutrition and after total parenteral nutrition. Am J Clin Nutr 35:(Suppl.), 1117–1127, 1982.

[5] Russell, DMcR, P J Prendergast, P L Darby, P E Garfinkel, J Whitwell and K N Jeejeebhoy. A comparison between muscle function and body composition in anorexia nervosa: the effect of refeeding. Am J Clin Nutr 38: 229–237, 1983.

[6] Collins J P, Oxby C B and Hill G L. Intravenous amino acids and intravenous hyperalimentation as protein-sparing therapy after major surgery-a controlled trial. Lancet 1:788–791, 1978.

[7] Almond D J, King R F G J, Surkinshaw L. Potassium depleton in surgical patients: Intracellular cation deficiency is independent of loss of body protein. Clin Nutr, 6:45–50, 1987

[8] Almond D J, King R F G J, Burkinshaw L, Laughland A. McMahon M J. Influence of energy source upon body composition in patients receiving intravenous nutrition. JPEN 13:471–477, 1989

[9] Fong C N, H L Atwood, K N Jeejeebhoy and M P Chariton. Nutrition and muscle potassium: differential effect in rat slow and fast muscles. Can J Physiol Pharmacol 65.218–2190 1987.

[10] Pichard C. E Hoshino, J P AJlard, M P Chariton, H L Atwood and K N Jeejeebhoy. Intracellular potassium and membrane potential in rat muscles during malnutrition and subsequent refeeding. Am J Clin Nutr 54:489–498, 1991.

[11] Newsholme E, Leech A R., eds. Biosynthesis of nucleic acids and proteins, Chap. 18. In: Biochemistry for the Medical Sciences, Chichester, J Wiley & Sons, 1983.

[12] Kammermeier H. High energy phosphate of the myocardium: concentration versus free energy. In: Cardiac Enegetics. Basic Research in Cardiology R.Jacob H.Just and C. Holubarsh eds. N.Y., Springer-Verlag 82(suppl. 2):31–36,1987.

[13] Pichard C, C Vaughan, R Struk, R L Armstrong and K N Jeejeebhoy. The effect of dietary manipulations (fasting, hypocaloric feeding and subsequent refeeding) on rat muscle energetics as assessed by nuclear magnetic resonance spectroscopy. J Clin Invest 82: 895–901, 1988.

[14] Mijan de ta Torre A, Madapallimattam A, Cross A, Armstrong R L, Jeejeebhoy K N. Effect of fasting, hypocaloric feeding and refeeding on the energetics of stimulated rat muscle as assessed by nuclear magnetic resonance spectroscopy. J Clin Invest 92:114–121, 1993.

[15] Ardawi M S Majzoub M F Masoud I M Newsholme E A. Enzymic and metabolic adaptations in the gastrocnemius, plantaris and soleus muscles of hypocaloric rats Biochemical Journal. 261(1):219–25. 1989.

[16] O'Brien, P. J., H. Shen, D. Bissonnette and K. N. Jeejeebhoy. Effects of hypocaloric feeding and refeeding on myocardial Ca and ATP cycling in the rat. Motec Cell Biochem 142:151–161, 1995.

[17] Godt R, Nosek T M Changes of intracellular milieu with fatigue or hypoxia depress contraction of skinned rabbit skeletal and cardiac muscle. J Physiol 412:155–180,1989.

[18] Wilkie D R. Shortage of chemical fuel as a cause of fatigue: studies by nuclear magnetic resonance and bicycle ergometry In: Human Muscle Fatigue: Physiological Mechanisms. Ciba Foundation Symposium 82. Eds. R Porter, J Whelan, London, Pitan Medical, 102–119,1981.

[19] Fromm A H L, Zimmer S D, Michurski S P, Mohankrishnan P, Ulstad V K, Thoma W J and Ugurbil K. Regulation of oxidative phosphorylation rate in intact cell. Biochemistry 29:3731–3743, 1990.

[20] McMillan J B and Pauly D F. Control of mitochondrial respiration. Mol and Cell Biiochem 81:121–129, 1988.

[21] Newsholme E A and Leech A R. Electron transfer chain In Biochemistry for the medical sciences J Wiley & sons Toronto, pp 113–149, 1983.

[22] BirchMachin M A, Briggs H L, Saborido A A, Bindoff L A, Tumbull D M. An evaluation of the measurement of the activities of complexes I–IV in the respiratory chain of human skeletal muscle mitochondria Biochemical Medicine and Metabolic Biology 51:3642, 1994.

[23] Krahenbuhl S, Talos C, Weismann U, Hoppel C L. Development and evaluation of spectrophotometric assay for complex III in isolated mitochondria, tissues and fibroblasts for rats and humans. Clin Chim Acta 230:177–187, 1994.

[24] Vallace D C. Disease of the mitochondnal DNA. Ann Rev Biochem 61:1175–1212, 1992.

[25] Hannavy K and Schatz R C. In Biochemistry of cell membranes. Eds. Papa s and Tager J M. Birkhauser Basel. pp 55–74, 1995.

[26] Virbasius J V and Scarpulla R C. Proc Natl Acad Sci 91:1309–1313, 1994.

[27] Antonetti D A, Reynet C, Kahn C R. Increased expression of mitochondrial-encoded genes in skeletal muscle of humans with diabetes mellitus. J Clin invest 95:1383–1388, 1995.

[28] Anderson S, Bankier A T, Barrell B G, de Bruijn MHL, Coulson A R, Drouin J, Eperon I C, Nierlich D P, Roe B A, Sanger F, Schreier P H, Smith A J H, Staden R, and Young I G. Sequenoe and organization of the human mitochondrial genome. Nature 290:457–465, 1981.

[29]Gadaleta G, Pepe G, De Candia G. Quagliariello C, Sbisa E, and Saccone C. The complete nucleotide sequence of the Rattus Norvegicus mitochondrial genome: cryptic signals revealed by comparative analysis between vertebrates. J Mol. Evol. 28:497–516, 1989.

[30]Ferrira G C and Pedersen P. J Sloenerg Biomembr 25:483–492, 1993.

[31]Papa S and Paradies P. Eur J Biochem 49:265–274, 1974.

[32]Martin M A, Molina J A, Jimenez-Jimenez F J, Benito-León J, Orti-Pareja M, Campos Y. Arenas J and the Grupo Centro de Trastomos del Movimiento. Respiratory-chain enzyme activities in isloated mitochondria of lymphocytes from untreated Parkinson's disease patients. Neurology 1996;46:1343–1346.

[33]L Lowry O. H., Rosebrough N. J., Farr Q. L. and Randall R. J. Protein measurement with the folin phenol reagent J. Biol. Chem. 1951;193:265–75.

[34]Krähenbühl S, Talos C, Ulrich W. Hoppel C L. Development and evaluation of a spectrophotometric assay for complex III in isolated mitochondria, tissues and fibroblasts from rats and humans, *Clinica Chimica Acta* 1994;230:177–87

[35]Capaldi R A, Marusich M F and Taanman J W. Mammalian cytochromevc oxidase: characterization of enzyme and immunological detection of subunits in tissue extracts and whole cells. Methods in Enzymology 1995;260:121–3.

What is claimed is:

1. A method for detecting malnutrition in a mammal, said method comprising:

measuring the activity of a mitochondrial enzyme complex selected from the group consisting of Complex I, Complex II and Complex III in a sample from a mammal, wherein decreased activity of said enzyme complex compared to that of a normal control sample is indicative of the presence of malnutrition in said mammal.

2. The method of claim 1, wherein said sample comprises lymphocytes.

3. The method of claim 1, wherein said sample comprises skeletal muscle.

4. The method of claim 1, wherein said sample is a blood sample.

5. The method of claim 1, wherein said mitochonddal enzyme complex is Complex I.

6. The method of claim 1, wherein said mitochondrial enzyme complex is Complex II.

7. The method of claim 1, wherein said mitochondrial enzyme complex is Complex III.

8. A method for evaluation of malnutrition in a mammal, comprising the steps of:

i) quantifying the activity of a mitochondrial enzyme complex selected from the group consisting of Complex I, Complex II and Complex III in a sample from a mammal and comparing the activity to a normal control sample; and ii) classifying said mammal as having or not having malnutrition.

9. The method of claim 8, wherein said mammal is classified as having malnutrition and the method further comprises the steps of restoring nutrition in said mammal and conducting a second assay quantifying the activity of said mitochondrial enzyme complex on a second sample from said mammal in order to determine whether the activity of said mitochondrial enzyme complex is restored.

10. The method of claim 8, wherein said control sample is sample matched for one or more criteria selected from the group consisting of age, sex and height.

11. A method for detecting the reversal of malnutrition in a malnutritioned mammal, said method comprising:

measuring the activity of a mitochondrial enzyme complex selected from the group consisting of Complex I, Complex II and Complex III in a first sample from said mammal, treating said mammal to restore nutrition; and conducting a second assay measuring the activity of said mitochondrial enzyme complex on a second sample from said mammal, wherein an increase in the activity of said enzyme complex compared to that of said first sample is indicative of the reversal of malnutrition in said mammal.

* * * * *